United States Patent
Kirk et al.

(10) Patent No.: US 10,488,413 B2
(45) Date of Patent: Nov. 26, 2019

(54) METHODS FOR TREATING PATIENTS AT RISK FOR COSTIMULATION BLOCKADE RESISTANT REJECTION WITH BELATACEPT

(71) Applicant: BRISTOL-MYERS SQUIBB COMPANY, Princeton, NJ (US)

(72) Inventors: Allan D Kirk, Durham, NC (US); Jaclyn Rae Espinosa, Durham, NC (US); Robert M Townsend, Garnet Valley, PA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 184 days.

(21) Appl. No.: 15/659,196

(22) Filed: Jul. 25, 2017

(65) Prior Publication Data
US 2017/0328903 A1    Nov. 16, 2017

Related U.S. Application Data

(63) Continuation of application No. 14/779,204, filed as application No. PCT/US2014/031945 on Mar. 27, 2014, now abandoned.

(60) Provisional application No. 61/806,206, filed on Mar. 28, 2013.

(51) Int. Cl.
*G01N 33/569* (2006.01)
*G01N 33/80* (2006.01)

(52) U.S. Cl.
CPC . *G01N 33/56972* (2013.01); *G01N 2800/245* (2013.01); *G01N 2800/52* (2013.01)

(58) Field of Classification Search
None
See application file for complete search history.

(56) References Cited

U.S. PATENT DOCUMENTS

2008/0160022 A1* 7/2008 Larsen ............ C07K 14/70521
424/133.1

FOREIGN PATENT DOCUMENTS

WO    WO 2006/108035 A1    10/2006

OTHER PUBLICATIONS

Chavez, H., et al., "Absence of CD4CD25 regulatory T cell expansion in renal transplanted patients treated in vivo with Belatacept mediated CD28-CD80/86 blockade", Transplant Immunology, 2007, vol. 17, No. 4, pp. 243-248.
Wojciechowski, David, et al., "Belatacept for prevention of acute rejection in adult patients who have had a kidney transplant: an update", Biologics:Targets and Therapy, 2012, vol. 6, pp. 385-393.
Espinosa, J., et al., "CD4+ T Cell Differentiation and Belatacept Resistant Rejection", American Transplant Congress, Meeting Abstracts, May 18, 2013, p. 44, Retrieved from the Internet: URL:http://www.atcmeetingabstracts.com/abstract/cd4-t-cell-differentiation-and-belatacept-resistant-rejection/.
Kinnear, et al., "Costimulation Blockade: Current Perspectives and Implications for Therapy", Transplantation (E-pub: Feb. 2013), vol. 95, pp. 527-535.
Sallusto, Federica, et al., Central Memory and Effector Memory T Cell Subsets: Function, Generation, and Maintenance, 2004, 22:745-63, Annu. Rev. Immunol.

* cited by examiner

*Primary Examiner* — Michelle F. Pauguio Frising
(74) *Attorney, Agent, or Firm* — Brian J. Walsh; Nickki L. Parlet

(57) ABSTRACT

The present invention provides methods utilizing changes in CD4+CD57+ T cells levels for determining the susceptibility of a transplant patient or patient in need thereof to costimulation blockade resistant rejection. These methods are useful for identifying effective drug regimens for the treatment of immune disorders associated with graft transplantation and/or maintenance of a transplant.

6 Claims, 8 Drawing Sheets

Specification includes a Sequence Listing.

Belatacept

FIG. 4

| Laser | 488 nm Blue | | | | 633 nm Red | | | 407 nm Violet | | | |
|---|---|---|---|---|---|---|---|---|---|---|---|
| filter-PMT | 530/3 | 575/26 | 780/60 | 660/20 | 710/50 | 780/60 | 450/50 | 660/40 | | | |
| Tube # | FITC | PE | PE-Cy7 | APC | Alexa 700 | APC-Alexa780 | V450 | Qdot 655 | PacOrange | | |
| 1 | CD57 1ul | PD1 5ul | CCR7 2ul | CD127 10ul | CD3 10ul* | CD8 1ul | CD4 2ul | CD45RA 1ul* | CD14\20 2ul\2ul | Memory |
| 2 | CD2 2ul | CD28 10ul | CCR7 2ul | CD27 10ul | CD3 10ul* | CD8 1ul | CD4 2ul | CD45RA 1ul* | CD14\20 2ul\2ul | Memory |
| 3 | CD11a 5ul | CD38 10ul | CCR7 2ul | HLADR 2ul | CD3 10ul* | CD8 1ul | CD4 2ul | CD45RA 1ul* | CD14\20 2ul\2ul | Activation |
| 4 | CD103 10ul | CD31 10ul | CCR7 2ul | CCR5 5ul | CD3 10ul* | CD8 1ul | CD4 2ul | CD45RA 1ul* | CD14\20 2ul\2ul | RTEs |
| 5 | CD39 2ul | CD25 5ul | CD127 5ul | | CD3 10ul* | | CD4 2ul | CD45RA 1ul* | CD14\20 2ul\2ul | Treg |
| 6 | IgD 10ul | IgM 10ul | CD19 1ul | IgG 20ul | CD27 10ul | CD24 5ul | CD5 5ul | CD38 5ul | CD3 5ul | B cells |
| 7 | Ki67 10ul | BCL2 10ul | CCR7 2ul | | CD3 10ul* | CD8 1ul | CD4 2ul | CD45RA 1ul* | CD14\20 2ul\2ul | Intracellular |
| 8 | Perforin 10ul | Gran B 2ul | CCR7 2ul | | CD3 10ul* | CD8 1ul | CD4 2ul | CD45RA 1ul* | CD14\20 2ul\2ul | Intracellular |

FIG. 5

```
ATGGGTGTACTGCTCACACAGAGGACGGCTGCTCAGTCTGGTCCTTGCACTCCTGTTTCCA        -19
M---G---V---L---L---T---Q---R---T---L---L---S---L---V---L---A---L---L---F---P---    -7

AGCATGGCGAGCATGGCAATGCACGTGGCCCCAGCCTGCTGTGGTACTGGCCAGCAGCCGA        +42
S---M---A---S---M---A---M---H---V---A---Q---P---A---V---V---L---A---S---S---R---   +14
   +1

GGCATCGCTAGCTTTGTGTGTGAGTATGCATCTCCAGGCAAATATACTGAGGTCCGGGTG        +102
G---I---A---S---F---V---C---E---Y---A---S---P---G---K---Y---T---E---V---R---V---   +34

ACAGTGCTTCGGCAGGCTGACAGCCAGGTGACTGAAGTCTGTGCGGCAACCTACATGATG        +162
T---V---L---R---Q---A---D---S---Q---V---T---E---V---C---A---A---T---Y---M---M---   +54

GGGAATGAGTTGACCTTCCTAGATGATTCCATCTGCACGGGCACCTCCAGTGGAAATCAA        +222
G---N---E---L---T---F---L---D---D---S---I---C---T---G---T---S---S---G---N---Q---   +74

GTGAACCTCACTATCCAAGGACTGAGGGCCATGGACACGGGACTCTACATCTGCAAGGTG        +282
V---N---L---T---I---Q---G---L---R---A---M---D---T---G---L---Y---I---C---K---V---   +94

GAGCTCATGTACCCACCGCCATACTACGAGGGCATAGGCAACGGAACCCAGATTTATGTA        +342
E---L---M---Y---P---P---P---Y---Y---E---G---I---G---N---G---T---Q---I---Y---V---   +114

ATTGATCCAGAACCGTGCCCAGATTCTGATCAGGAGCCCAAATCTTCTGACAAAACTCAC        +402
I---D---P---E---P---C---P---D---S---D---Q---E---P---K---S---S---D---K---T---H---   +134

ACATCCCCACCGGTCCCCAGCACCTGAACTCCTGGGGGGATCGTCAGTGTTCCTCTTCCCC       +462
T---S---P---P---S---P---A---P---E---L---L---G---G---S---S---V---F---L---F---P---   +154

CCAAAACCCAAGGACACCCTCATGATCTCCCGGACCCCTGAGGTCACATGCGTGGTGGTG       +522
P---K---P---K---D---T---L---M---I---S---R---T---P---E---V---T---C---V---V---V---   +174

GACGTGAGCCACGAAGACCCTGAGGTCAAGTTCAACTGGTACGTGGACGGCGTGGAGGTG       +582
D---V---S---H---E---D---P---E---V---K---F---N---W---Y---V---D---G---V---E---V---   +194

CATAATGCCAAGACAAAGCCGCGGGAGGAGCAGTACAACAGCACGTACCGTGTGGTCAGC       +642
H---N---A---K---T---K---P---R---E---E---Q---Y---N---S---T---Y---R---V---V---S---   +214

GTCCTCACCGTCCTGCACCAGGACTGGCTGAATGGCAAGGAGTACAAGTGCAAGGTCTCC       +702
V---L---T---V---L---H---Q---D---W---L---N---G---K---E---Y---K---C---K---V---S---   +234

AACAAAGCCCTCCCAGCCCCCATCGAGAAAACCATCTCCAAAGCCAAAGGGCAGCCCCGA       +762
N---K---A---L---P---A---P---I---E---K---T---I---S---K---A---K---G---Q---P---R---   +254

GAACCACAGGTGTACACCCTGCCCCCATCCCGGGATGAGCTGACCAAGAACCAGGTCAGC       +822
E---P---Q---V---Y---T---L---P---P---S---R---D---E---L---T---K---N---Q---V---S---   +274

CTGACCTGCCTGGTCAAAGGCTTCTATCCCAGCGACATCGCCGTGGAGTGGGAGAGCAAT       +882
L---T---C---L---V---K---G---F---Y---P---S---D---I---A---V---E---W---E---S---N---   +294

GGGCAGCCGGAGAACAACTACAAGACCACGCCTCCCGTGCTGGACTCCGACGGCTCCTTC       +942
G---Q---P---E---N---N---Y---K---T---T---P---P---V---L---D---S---D---G---S---F---   +314

TTCCTCTACAGCAAGCTCACCGTGGACAAGAGCAGGTGGCAGCAGGGGAACGTCTTCTCA      +1002
F---L---Y---S---K---L---T---V---D---K---S---R---W---Q---Q---G---N---V---F---S---   +334

TGCTCCGTGATGCATGAGGCTCTGCACAACCACTACACGCAGAAGAGCCTCTCCCTGTCT      +1062
C---S---V---M---H---E---A---L---H---N---H---Y---T---Q---K---S---L---S---L---S---   +354

CCGGGTAAATGA
P---G---K---*
```

METHODS FOR TREATING PATIENTS AT RISK FOR COSTIMULATION BLOCKADE RESISTANT REJECTION WITH BELATACEPT

CROSS-REFERENCE TO RELATED APPLICATIONS

This application is a continuation of U.S. patent application Ser. No. 14/779,204, filed Sep. 22, 2015, now abandoned, which is the 371 of International Application No. PCT/US2014/31945, filed Mar. 27, 2014, now published, which claims priority to U.S. Provisional Application No. 61/806,206, filed Mar. 28, 2013; the entire content of which is incorporated herein by reference.

Throughout this application various publications are referenced. The disclosures of these publications in their entireties are hereby incorporated by reference into this application in order to more fully describe the state of the art to which this invention pertains.

FIELD OF THE INVENTION

This invention relates to methods for determining the susceptibility of a transplant patient to costimulation blockade resistant rejection. These methods are useful for identifying effective drug regimens for the treatment of immune disorders associated with graft transplantation and/or maintenance of a transplant.

SEQUENCE LISTING

Applicants enclose herewith the "SEQUENCE LISTING" for the above-captioned application in ASCII format via EFS-Web and is hereby incorporated by reference in its entirety. The ASCII copy, created on Sep. 22, 2015, is named SEQ.txt and is 6 kilobytes in size. The information contained in the attached "SEQUENCE LISTING" is identical to the information in the specification as originally filed. No new matter is added.

BACKGROUND OF THE INVENTION

Given the central role of T-cells in transplant rejection, a common goal among current immunosuppressive therapies is to block T-cell activation and function (Sayegh, M. H. et al., *N. Engl. J. Med.*, 338(25):1813-1821 (1998)). T-cells require both an antigen-specific (Signal 1) and co-stimulatory signal (Signal 2) for full activation (Lenschow, D. J. et al., *Annu. Rev. Immunol.*, 14:233-258 (1996)). One of the best-characterized co-stimulatory pathways involves the CD28-CD80/86 (B7-1/2) interaction (Linsley, P. S. et al., *Annu. Rev. Immunol.*, 11:191-212 (1993)). Cytotoxic T-lymphocyte antigen 4 (CTLA4) binds to CD80/86 with higher avidity than CD28, and is transiently expressed on T-cells following their activation, where it interrupts the interaction between CD28 and CD80/86 (Oosterwegel, M. A. et al., *Curr. Opin. Immunol.*, 11(3):294-300 (1999)). This creates a negative feedback signal for T-cell activation.

Functionally distinct T cell populations can be defined by the expression of specific cell surface antigens. Numerous studies describe associations between T cell surface phenotype and function (Appay, V. et al., *Nat. Med.*, 8:379-385 (2002)). CD57, a surface molecule expressed on T and NK cells, is a marker with functional associations. CD57 has been commonly described as an external marker of cell senescence, a state in which the cell is in persistent cell cycle arrest. Expansions of CD4+ T cells expressing CD57 have been associated with a number of chronic pathological conditions such as tuberculosis, malaria, rheumatoid arthritis, and HIV-1 infection (Maeda, T. et al., *Arthritis Rheum.*, 46:379-384 (2002); Imberti, L. et al., *Blood*, 89:2822-2832 (1997)).

Belatacept (L104EA29YIg) is the first biologic agent approved for primary maintenance immunosuppression, selectively blocking the CD28 co-stimulation pathway to prevent T-cell activation (Larsen, C. P. et al., *Am. J. Transplant.*, 5:443-453 (2005)). Belatacept combined with corticosteroids and a mycophenolic acid is indicated for prophylaxis of graft rejection in adults receiving a renal transplant. While Belatacept has been associated with improved long-term graft function as well as patient and graft survival, patients treated with this costimulation blockade molecule tended to experience early acute rejection.

Further, while the introduction of kidneys from extended criteria donors has been necessary to alleviate donor organ shortages, recipients are at greater risk of complications and graft loss than recipients of living or standard criteria deceased donor kidneys (Tullius, S. G. et al., *Eur. Renal Dis.*, 1:51-54 (2007)).

With the increasing use of costimulation blockade molecules and higher risk extended criteria donor organs, it is clear that there is a need to prospectively identify patients at risk for costimulation blockade resistant rejection. The Inventors have identified a CD4+ T cell phenotype that strongly correlates with risk for costimulation blockade resistant rejection.

At present, there are no predictive assays to identify patients at risk of costimulation blockade resistant rejection. Thus, there is a need in the art for a diagnostic assay that could determine whether a patient would be eligible to be treated with costimulation blockade molecules or at risk of acute rejection. The present invention provides such novel assay.

SUMMARY OF INVENTION

In one aspect, the invention provides a method of predicting if a transplant patent is at risk of costimulation blockade resistant rejection, the method comprising: (a) acquiring a blood sample from a person receiving costimulation blockade therapy, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

In another aspect, the invention provides a method of predicting if a patient in need of a transplant is at risk of costimulation blockade resistant rejection, the method comprising: (a) acquiring a peripheral blood sample from a person prior to transplantation, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

BRIEF DESCRIPTION OF THE FIGURES

FIG. 4 shows the phenoflow panels utilized in Example 1. *CD3 antibody was diluted 1:8 before use, while the CD45RA antibody was diluted 1:10 before use.

FIG. 5 (SEQ ID NOS: 1 and 2) depicts a nucleotide and amino acid sequence of L104EA29YIg, a CTLA4 mutant molecule comprising a signal peptide; a mutated extracellular domain of CTLA4 starting at methionine at position +1 and ending at aspartic acid at position +124, or starting at alanine at position −1 and ending at aspartic acid at position +124; and an Ig region. SEQ ID NOS: 1 and 2 depict a nucleotide and amino acid sequence, respectively, of L104EA29YIg, a CTLA4 mutant molecule, comprising a signal peptide; a mutated extracellular domain of CTLA4 starting at methionine at position +27 and ending at aspartic acid at position +150, or starting at alanine at position +26 and ending at aspartic acid at position +150; and an Ig region.

DETAILED DESCRIPTION OF THE INVENTION

Definitions

Figure 1:
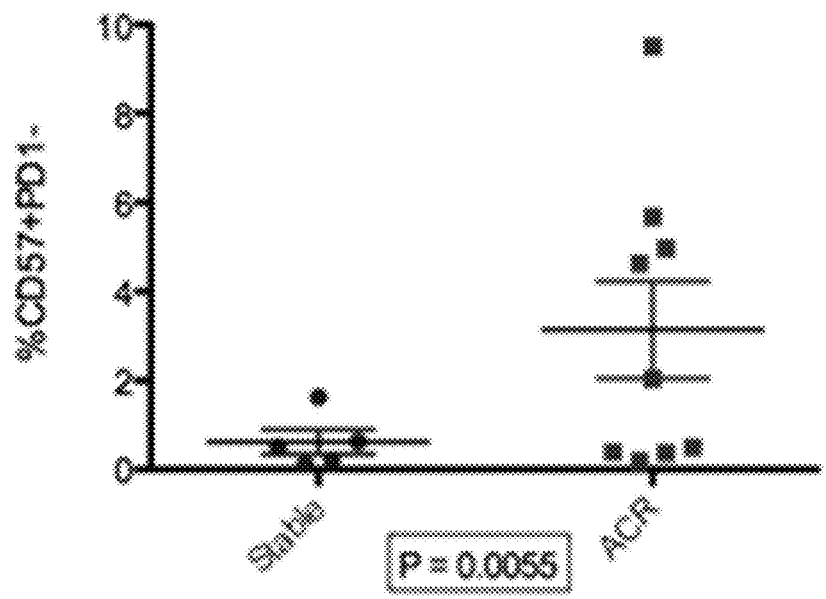
FIG. 1 shows a graph of PBMCs from belatacept treated patients examined for markers of senescence (CD57) and exhaustion (PD1). Patients who experienced ACR had a significantly higher percentage of CD57+PD1− cells in the CD4+, but not CD8+, compartment. These differences were significant in each memory subset of CD4+, but not CD8+, T cells. TCM denotes Central Memory T cells; TEM denotes Effector Memory T cells; TEMRA denotes Terminally Differentiated Effector Memory T cells.
Figure 1:
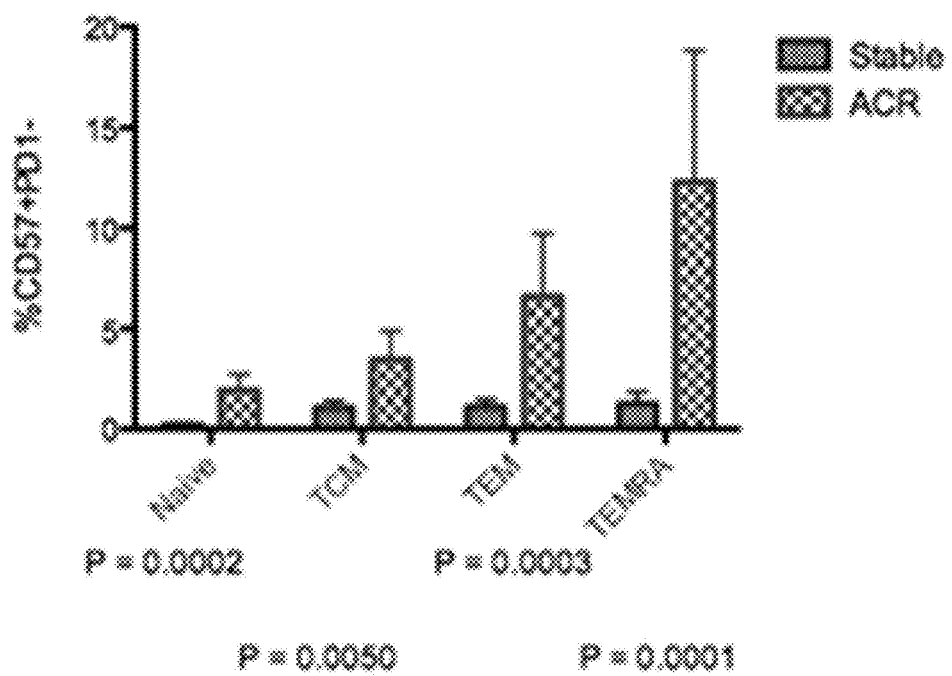
Figure 1:
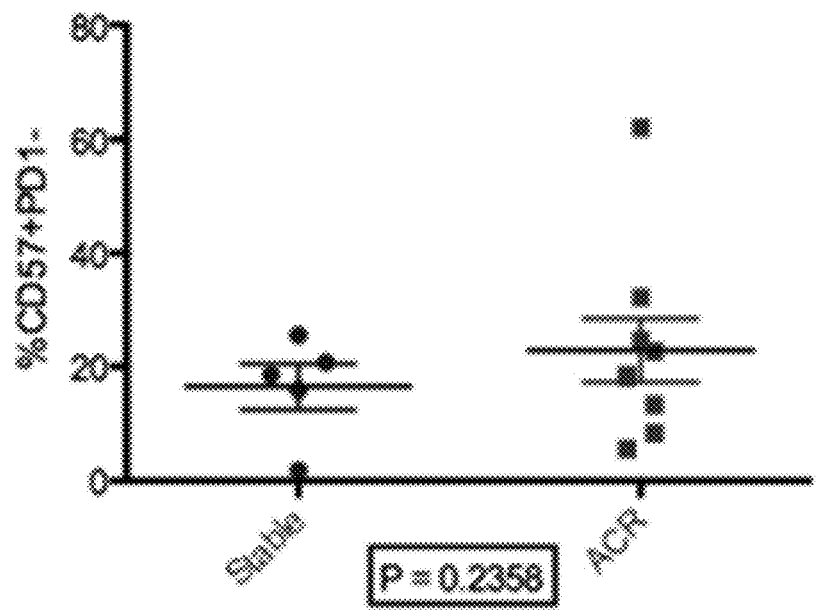
Figure 1:
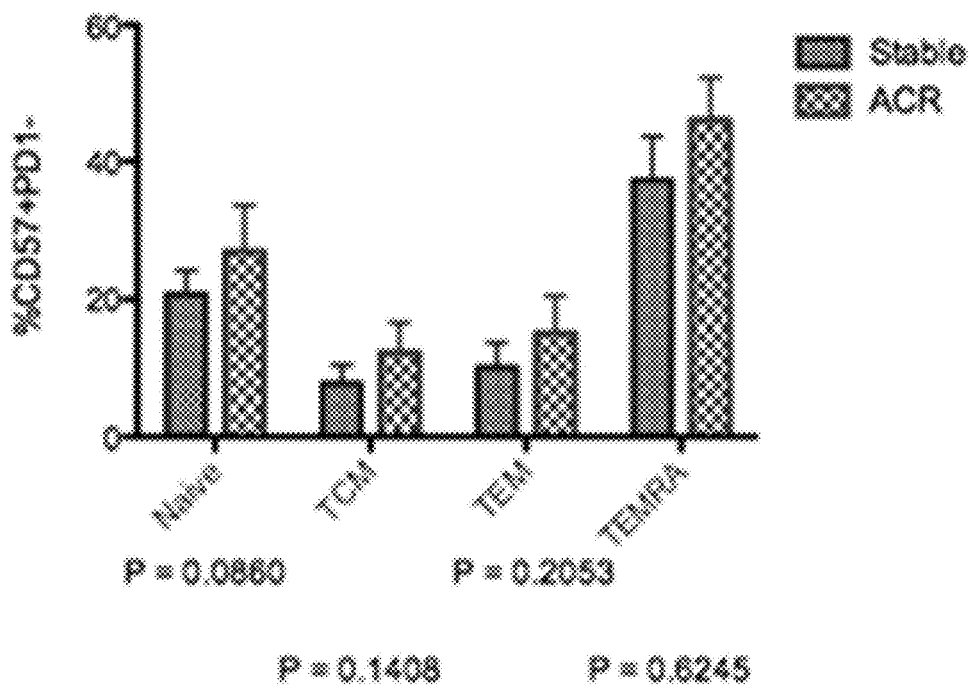
Figure 2:
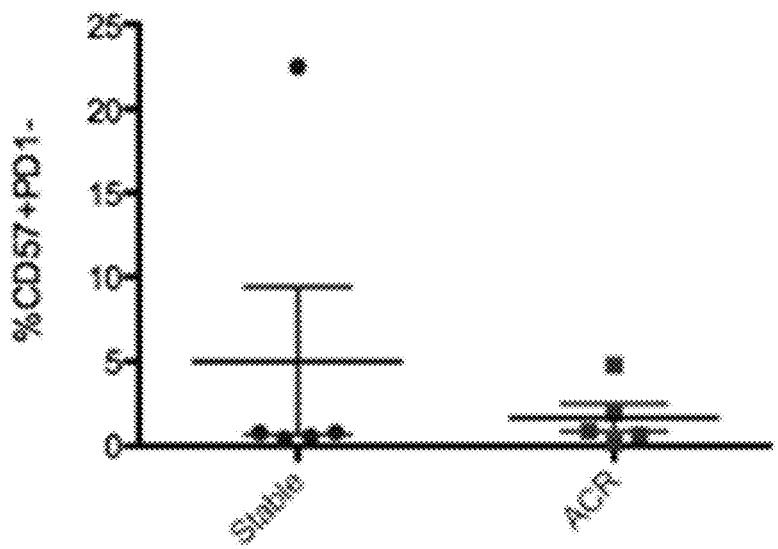
FIG. 2 shows a graph of PBMCs from tacrolimus treated patients examined for markers of senescence (CD57) and exhaustion (PD1). No significant correlations with outcome were found in the CD57+PD1- compartment of either CD4+ or CD8+T cells. TCM denotes Central Memory T cells; TEM denotes Effector Memory T cells; TEMRA denotes Terminally Differentiated Effector Memory T cells.
Figure 2:
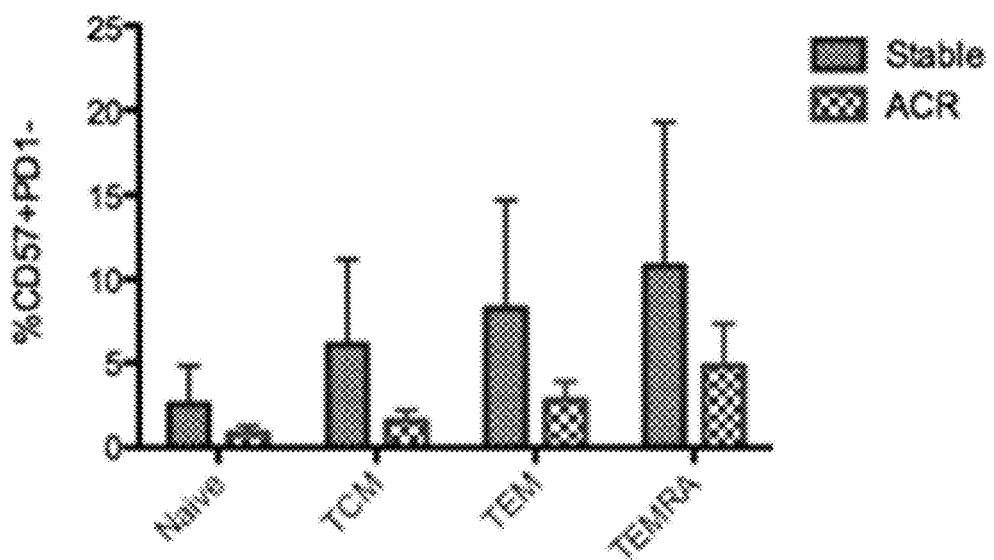
Figure 2:
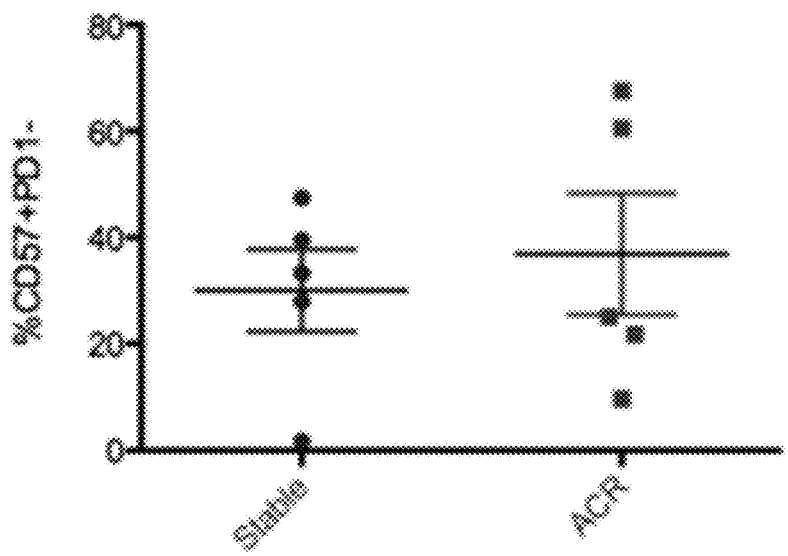
Figure 2:
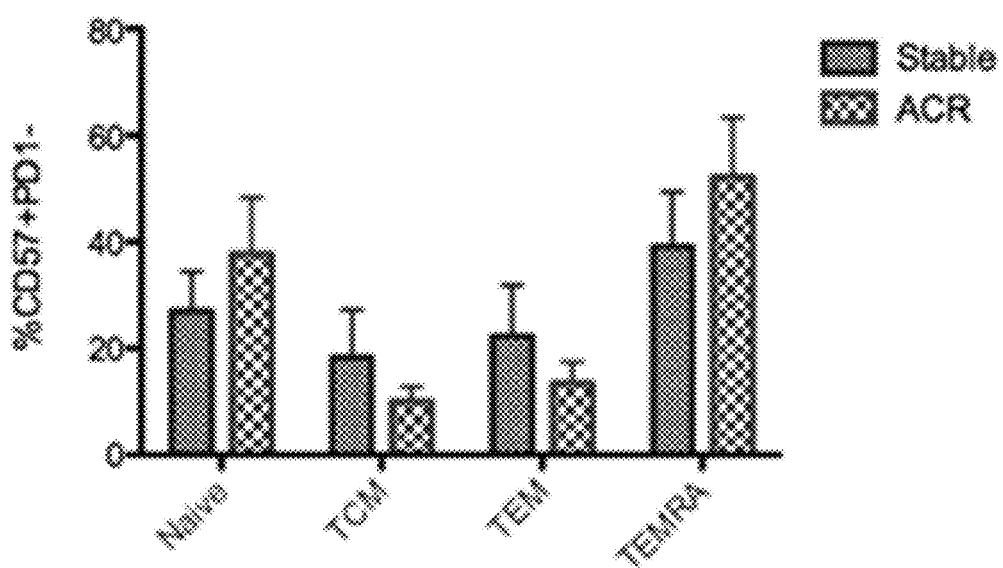
Figure 3:
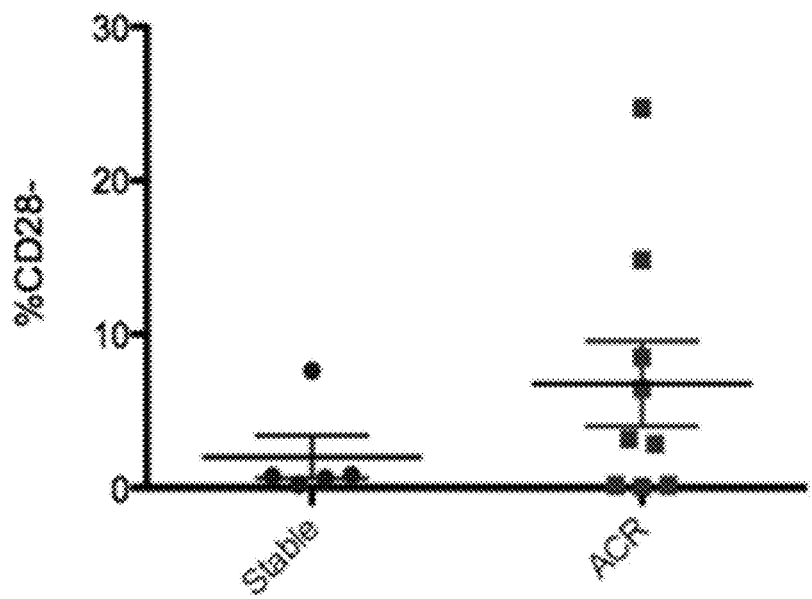
FIG. 3 shows that CD28– T cells do not predict acute cellular rejection outcome. PBMCs from belatacept and tacrolimus treated patients were examined for surface expression of costimulation markers CD28 and CD27. A trend existed towards increased prevalence of CD28 negative CD4 T cells in the belatreated patients who rejected, but this did not reach statistical significance. No correlations between CD28 expression on CD8 cells and outcome were observed.
Figure 3:
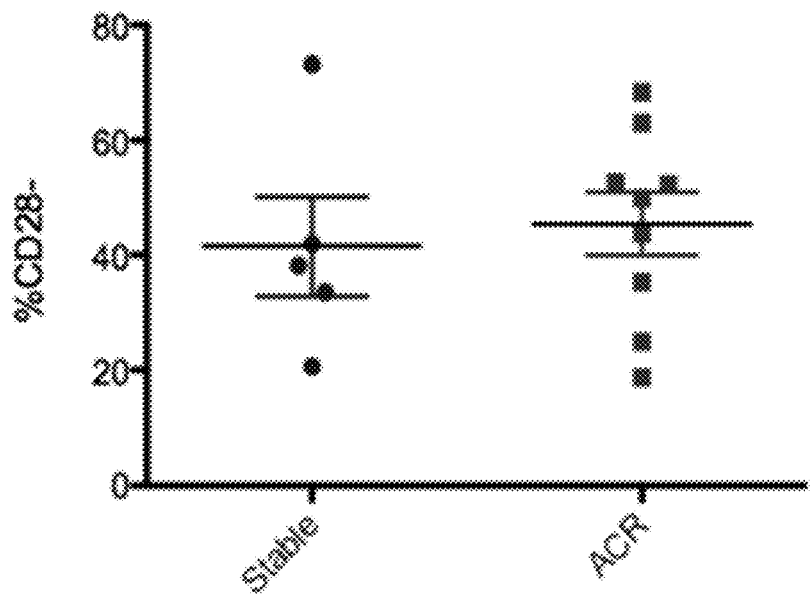
Figure 3:
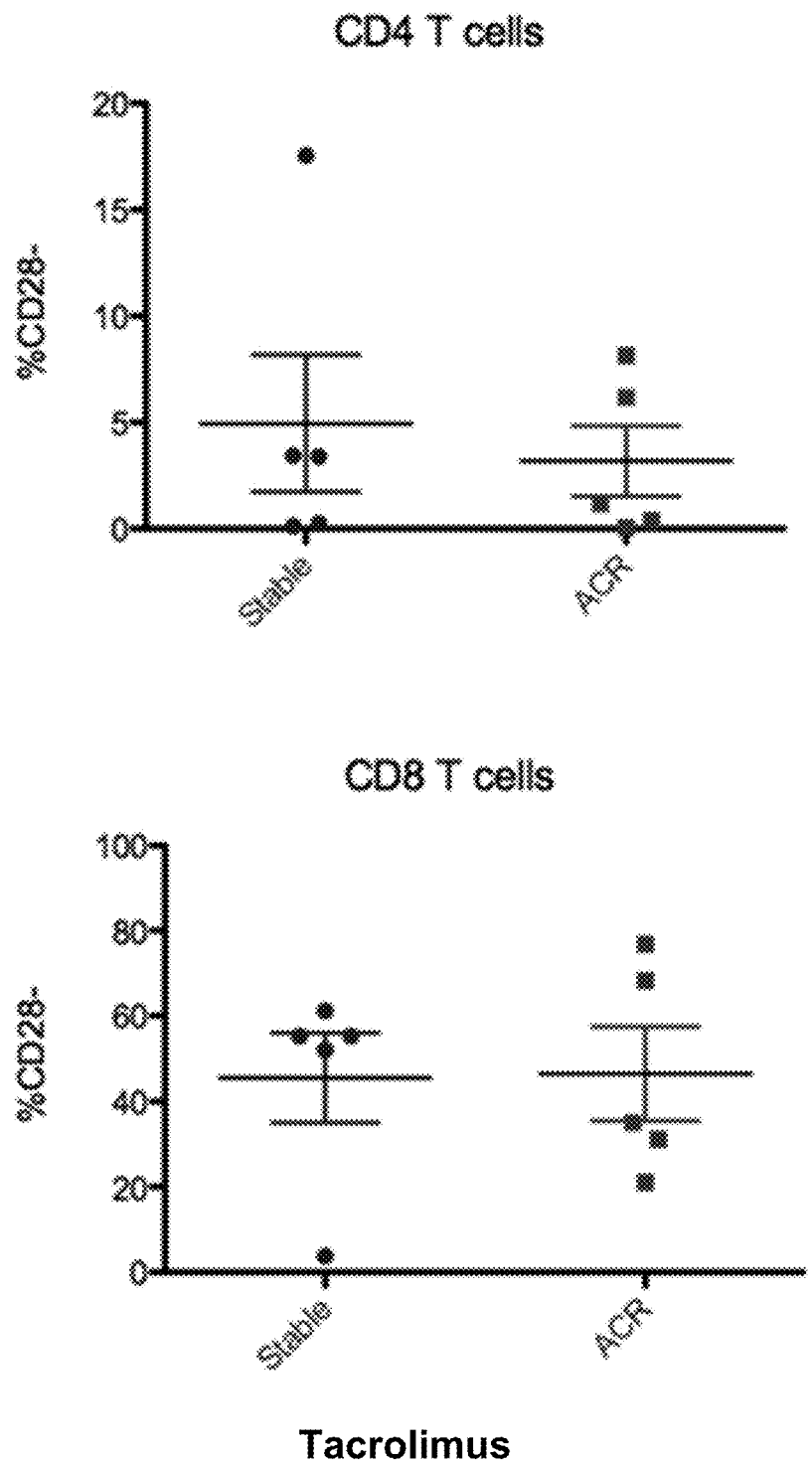

All scientific and technical terms used in this application have meanings commonly used in the art unless otherwise specified. As used in this application, the following words or phrases have the meanings specified.

As used herein, "ligand" refers to a molecule that specifically recognizes and binds another molecule, for example, a ligand for CTLA4 is a B7 molecule.

"L104EA29YIg", "belatacept" and "LEA29YIg" are used interchangeable herein and refer to a fusion protein that is a soluble CTLA4 mutant molecule comprising an extracellular domain of wildtype CTLA4 with amino acid changes A29Y (a tyrosine amino acid residue substituting for an alanine at position 29) and L104E (a glutamic acid amino acid residue substituting for a leucine at position +104), joined to an Ig tail (included in FIG. 4, SEQ ID NOS: 1 and 2; DNA encoding L104EA29YIg was deposited on Jun. 20, 2000 with ATCC® number PTA-2104. Belatacept is commercially available as the IV formulation, NULOJIX® (Bristol-Myers Squibb Company). Belatacept is a fusion protein that acts as a selective costimulation blocker by binding surface ligands (CD80 and CD86) on antigen-presenting cells. In antigen recognition, the binding of the costimulation receptor on T cells (CD28) to CD80 and CD86 (signal 2) is required for efficient T-cell activation when the T-cell receptor encounters MHC alloantigens (signal 1).

As used herein, "B7" refers to the B7 family of molecules including, but not limited to, B7-1 (CD80), B7-2 (CD86) and B7-3 that may recognize and bind CTLA4 and/or CD28.

As used herein, the term "CD4" refers to "cluster of differentiation 4" which is a glycoprotein expressed on the surface of T helper cells, monocytes, macrophages, and dendritic cells As used herein, "CD57+ T cells" are T cells with CD57 molecules expressed on the cell surface.

As used herein, to "block" or "inhibit" a receptor, signal or molecule means to interfere with the activation of the receptor, signal or molecule, as detected by an art-recognized test. Blockage or inhibition may be partial or total. For example, blockage of a cell-mediated immune response can be detected by determining the functionality of the transplant, such as the serum creatinine concentrations following renal transplantation.

As used herein, "costimulation blockade resistant rejection" and "acute rejection" are used interchangeable herein and refer to a reaction against allograft or xenograft tissue that is incompatible with the recipient, which typically occurs 2 to 60 days after transplantation.

As used herein, "treat" or "treating" a disorder or disease means to manage a disease or disorder by medicinal or other therapies. Treatment of a disease or disorder may suppress immune-mediated events associated with a disease, ameliorate the symptoms of a disease or disorder, reduce the severity of a disease or disorder, alter the course of disease or disorder progression and/or ameliorate or cure the basic disease or disorder problem. For example, to treat an immune disorder associated with graft transplantation may be accomplished by regulating an immune response e.g., by regulating functional CTLA4- and/or CD28-positive cell interactions with B7-positive cells. For example, treating renal transplant rejection includes inhibition of renal transplant rejection as measured by glomerular filtration rate (GFR). For example treating immune disorders associated with graft transplantation includes prophylaxis of organ rejection by administration of L104EA29YIg. Further, treating immune disorders associated with graft transplantation may prolong the survival of the host and transplanted organ.

As used herein, "immune disorders associated with graft transplantation" means any transplant related disease mediated by T-cell interactions with B7-positive cells including, but not limited to, immune disorders associated with graft transplantation rejection, graft related disorders, graft versus host disease (GVHD) (e.g., such as may result from bone marrow transplantation, or in the induction of tolerance), rejection of the graft or transplant including acute rejection of the graft or transplant and chronic rejection of the graft or transplant.

As used herein, the "graft" or "transplant" may be solid organ allografts or xenografts, tissue or cell allografts or xenografts or external anatomy allografts or xenografts, including but not limited to skin, islet cells (also known as islets), muscles, hepatocytes, neurons, heart, liver, kidney, lung, appendages, limbs, nose, ear or face.

Early costimulation blockade resistant rejection has been seen in some patients on costimulation blockade immunosuppression, such as belatacept. Hypothesizing that T cell phenotype might prospectively identify patients at risk for costimulation blockade resistant rejection, transplant patients receiving costimulation blockade, were studied by specifically quantifying terminally differentiated memory cells expressing CD57, a marker of T cell senescence, and relating this expression to clinical outcome (see Example 1).

As discussed in Example 1, peripheral blood samples were obtained from kidney transplant patients prior to drug administration and analyzed by multiparameter flow cytometry, specifically analyzing the samples for markers of memory, differentiation, activation, exhaustion and senescence. Patients who eventually experienced acute rejection had a markedly higher percentage of CD4+CD57+PD1− T cells (p=0.0055) at the time of transplantation compared to patients without rejection (FIG. 1). Although typically considered a marker of senescence, CD57 expression on CD4+ T cells was paradoxically correlated with expression of the proliferation marker Ki67 (p=0.0087), and was not associated with shorter telomere length (p=0.7424). These relationships were limited to the CD4 compartment. CD8+CD57+ T cells marginally trended higher in acute rejection patients (p=0.2358, FIG. 1), but CD57 expression on CD8+ T cells was associated with more traditional indices of senescence including reduced Ki67 expression and shorter telomere length.

In one aspect, the invention provides a method of predicting if a transplant patent is at risk of costimulation blockade resistant rejection, the method comprising: (a) acquiring a blood sample from a person receiving costimulation blockade therapy, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

In another aspect, the invention provides a method of predicting if a patient in need of a transplant is at risk of costimulation blockade resistant rejection, the method comprising: (a) acquiring a peripheral blood sample from a person prior to transplantation, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

In one embodiment, the invention provides a method of predicting if a kidney transplant patent is at risk of costimulation blockade resistant rejection, the method comprising: (a) acquiring a blood sample from a person receiving costimulation blockade therapy, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

In one embodiment, the invention provides a method of predicting if a patient in need of a kidney transplant is at risk of costimulation blockade resistant rejection, the method comprising: (a) acquiring a peripheral blood sample from a person prior to transplantation, (b) quantitating the percent of CD+CD57+ T cells and (c) comparing the percentage of CD4+CD57+ T cells in the test sample with the percentage of CD4+CD57+ T cells in a reference, wherein the percentage of CD4+CD57+ T cells in the test sample is elevated compared to a reference.

In one embodiment, the reference may be blood from normal healthy controls or stable transplant patients; or a reference value determined from a representative number of normal healthy controls or stable transplant patients.

In another embodiment the percentage of CD4+CD57+ T cells is elevated at least 2 fold, from 2 to 25 fold, from 2 to 20 fold, from 2 to 15 fold, from 2 to 10 fold, from 2 to 5 fold compared to the percentage of CD4+CD57+ T cells in a reference.

In another embodiment the CD4+CD57+ T cell content of the blood sample is measured by flow cytometry. Flow cytometry has been used with increasing regularity in clinical laboratories for immunophenotyping. The advantages of flow cytometry include speed, sensitivity, precision and objectivity. The components and operation of flow cytometers is well known to those skilled in the art and will not be described in detail herein. For purposes of a description of such, applicants refer to U.S. Pat. No. 5,567,627, issued Oct. 22, 1996 which is incorporated herein by reference in its entirety.

It is sufficient to indicate that the components and methodology of flow cytometry can be used to provide specific information on a number of parameters of a sample. For example it is possible to provide information on components of different sizes within a sample, while simultaneously providing information on signals of different wavelengths received from different components received from the sample. Thus, when a sample includes components of varying sizes and also includes components with labels which emit different wavelengths of light the flow cytometry data obtained can provide multidimensional information to the user. The present invention utilizes this technology by providing different types of labeled antibodies and labeled and unlabelled cells expressing known antigens. By exposing a sample to such and thereafter analyzing such within a flow cytometer it is possible to obtain substantial amounts of information regarding the blood in a quick and efficient manner.

Multiparameter flow cytometry is the method of choice, when immunophenotyping is desired, because more information can be objectively obtained from fewer cells due to the use of antibodies to differentiation-associated antigens and antibodies to activation-associated antigens at the same time to define what functions specific populations of cells are performing. For example, multi-color fluorescence-activated cell sorter analysis can be performed by obtaining peripheral blood samples from patients and normal healthy controls by hemolysis using the Whole Blood Lysing Reagent Kit (Beckman Coulter, Fullerton, Calif.). Cell surface antigens of peripheral blood leukocytes can be detected using a FACS®Calibur flow cytometer with the CELLQuest program (Becton Dickinson, Mountain View, Calif.). Cell surface antigens and intracellular cytokines can be detected using fluor-labeled monoclonal antibodies, typically available from Becton Dickinson.

Cell stimulation and staining for intracellular cytokine analysis can be performed according to the manufacturer's instructions (PharMingen, San Diego, Calif.). Briefly, peripheral blood leukocytes are stimulated with phorbol myristate acetate and calcium ionophore for 4 hours. For the last 3 hours of stimulation, the intracellular transport inhibitor, nomensin (GOLGISTOP®) is added for accumulation of intracellular cytokines. Afterward, cell surface antigens are stained with fluorescent-labeled monoclonal antibodies specific for the desired antigen. After CYTOFIX®/CYTOPERM® solution is added to fix and permeabilize the cells, intracellular cytokines are stained with fluorescent-labeled monoclonal antibodies and multi-color fluorescence-activated cell sorter (FACS) analysis is performed.

In a further embodiment, the costimulation blockage therapy comprises administering L104EA29YIg (belatacept), a mutant CTLA4Ig molecule, which is a fusion protein that acts as a selective costimulation blocker by binding surface ligands (CD80 and CD86) on antigen-presenting cells.

The typical belatacept pharmaceutical composition exemplified in the instant invention is an intravenous (i.v.) formulation listed below.

Composition of Lyophilized L104EA29YIg 100 mg/Vial Drug Product

| Component | Amount/Vial (mg)[a] |
|---|---|
| L104EA29YIg | 110[a] |
| Sucrose | 220 |
| Sodium Phosphate Monobasic Monohydrate | 15.18 |
| Sodium Chloride | 2.55 |
| 1N Sodium Hydroxide | Adjust to pH 7.5 |
| 1N Hydrochloric Acid | Adjust to pH 7.5 |

[a]Each vial contains 10% overfill for vial, needle and syringe holdup of the reconstituted solution.

The lyophilized drug is typically reconstituted to about 25 mg/ml with 10 ml of either Sterile Water for Injection, USP (SWFI) or 0.9% Sodium Chloride Injection, USP. The reconstituted solution is further diluted to drug product concentrations between 1 and 10 mg/ml with 0.9% Sodium Chloride Injection, USP. The diluted drug product for injection is isotonic and suitable for administration by intravenous infusion.

L104EA29Y is typically administered at 10 mg/kg weight of the patient during the early phase, high risk period that follows transplantation and decreased to 5 mg/kg weight of the patient for a maintenance dosage.

Typical target trough serum concentration of L104EA29Y are between about 3 μg/mL and about 30 μg/mL over the first 3 to 6 months post-transplant which is sufficient to maintain function of the allograft, preferably between about 5 μg/mL and about 20 μg/mL. Typically, target trough serum concentration of L104EA29Y during the maintenance phase are between about 0.2 μg/mL and about 3 μg/mL, preferably between about 0.25 μg/mL and about 2.5 μg/mL.

A typical administration regimen includes an early phase, in which doses are higher and the frequency of administration is increased during the period of greatest immunologic risk, followed by a maintenance phase. The early phase regimen may range from the first 3 to 6 months post-transplantation and involves administration that initially is more frequent than monthly, preferably as frequently as daily, weekly or every two weeks depending on the immunologic risk and/or target trough serum concentration. The maintenance phase begins when the early phase ends and involves administration that is not more frequent than monthly, and lasts for as long as needed, typically for as long as the patient retains the transplant. As used herein, day 1 is defined as the day of the transplant or the first day of treatment with L104EA29Y or pharmaceutical compositions thereof.

The dosage of L104EA29Y in the early phase is about 8 to about 12 mg/kg weight of the patient, preferably about 10 mg/kg. The dosage of L104EA29YIg of the invention in the maintenance phase is about 3 to about 7 mg/kg weight of the patient, preferably about 5 mg/kg.

The early phase may range from the first 3 to 6 months post-transplantation. The administration regimen during early phase may vary depending on the status of the recipient and/or graft. For example, a more intensive early phase regimen would administer a higher dose of the molecules or the pharmaceutical compositions of the invention on day 1, day 5, week 2 visit (e.g., day 13-17), then every two weeks for the first 3 months (e.g., on week 4 visit, week 6 visit, week 8 visit, week 10 visit, and week 12 visit), followed by monthly administration through month 6 visit (e.g., on month 4 visit, month 5 visit, and month 6 visit). An example of a typical more intensive early phase regimen is administration of 10 mg/kg weight of the patient of L104EA29YIg at days 1, 5, 15, 29, 43, 57, 71, 85, 113, 141 and 169. A less intensive regimen, for example, would administer the molecules or the pharmaceutical compositions of the invention on day 1, week 2 visit, week 4 visit, then monthly through month 3 visit. An example of a typical less intensive early phase regimen is administration of 10 mg/kg weight of the patient of L104EA29YIg on days 1, 15, 29, 57 and 85.

Typically, an early phase is followed by a maintenance phase where lower doses of the molecules or pharmaceutical compositions of the invention are administered at one to two month intervals for as long as needed, typically for as long as the patient retains the transplant. An example of the maintenance phase for the more intensive regimen described above includes monthly administration of 5 mg/kg weight of the patient of L104EA29YIg starting at month 7 visit. While an example of the maintenance phase for the less intensive regimen above would include monthly administration of 5 mg/kg weight of the patient of L104EA29YIg starting at month 4 visit.

Alternatively, one knowledgeable in the art would be able to modify the administration regimen in response to the patients risk status and/or response to the therapy post transplantation. For example, the early phase of the less intensive regimen described above could be modified by adding administration day 5 to the regimen, thereby increasing the frequency of administration during the period of greatest immunologic risk.

As used herein, "four weeks", "month", "months" or "monthly" refers to a period of 28±5 days. As used herein, "two weeks" refers to a period of 14±3 days.

Flexibility in the administration regimens is required to facilitate administration scheduling in the lives of transplant recipients, while maintaining the target trough profile of L104EA29Y. Permitted windows for administering the doses may be as follows:

| Visit | Visit window |
|---|---|
| Day 1 and day 5 | 96 hours apart ± 6 hours |
| Week 2 | Target date ± 2 days |
| Week 4-Month 6 | Target date ± 3 days |
| from Month 7 thereafter | Target date ± 5 days |

The target date is a result of adding the desired duration to the previous actual visit date. The desired duration for the week 2 visit is 10 days. The desired duration is 14 days for a visit planned for two weeks from the previous visit, e.g., a week 6 visit following a week 4 visit. The desired duration is 28 days for a visit planned for a month or four week from the previous visit, e.g., a month 4 visit following a month 3 visit. The desired duration is 56 days for a visit planned for two months from the previous visit, e.g., a month 8 visit after a month 6 visit. For example, a day 15 actual visit date plus 14 days results in a week 4 target date of day 29. Based on the visit windows above, the administration may occur on day 29±3 days. Should the administration occur on day 26, that day becomes the actual visit date utilized for the calculation of the next target date.

Low risk of acute rejection recipients typically include those who receive transplants from living related donors and well matched recipient/donors. High risk of acute rejection recipients typically include those who receive transplants from marginal donors or re-transplants, have high panel reactive antibodies or are African American.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

EXAMPLE 1

Early costimulation blockade resistant rejection has been seen in some patients on belatacept-based immunosuppression. Hypothesizing that T cell phenotype might prospectively identify patients at risk for costimulation blockade resistant rejection, patients receiving belatacept-based costimulation blockade, were studied by specifically quantifying terminally differentiated memory cells expressing CD57, a marker of T cell senescence, and relating this expression to clinical outcome.

Methods: Samples from renal allograft recipients receiving belatacept-based immunosuppression were selected from an IRB-approved tissue acquisition protocol.

Study Population:

Organ transplant recipients, candidates for organ transplantation, and their organ donors under evaluation at the Emory University Hospital/Emory Transplant Center (Emory) or Children's Healthcare of Atlanta (CHOA) were considered for study.

Inclusion Criteria:
  Recipients of or candidates for organ transplantation or organ donors for recipients under evaluation at Emory or CHOA.
  Normal volunteers to include individuals without any known end-stage organ disease who are not on any immunosuppressive medication, and individuals with conditions requiring immunosuppression (such as dermatological diseases) that do not require transplant therapies.

Exclusion Criteria:
  Patients who fail to meet the criteria for transplantation or post transplant follow-up by Emory or CHOA physicians.
  Any condition that, in the opinion of the attending physician, would place the patient at undue risk by participating. Specific conditions include but are not limited to anemia prohibitive of phlebotomy, coagulopathy or technical considerations that would prevent acquisition of sufficient tissue on biopsy for clinical use, or medical urgency preventing timely administration of the consenting process.

Enrollment

Volunteers were recruited for each of the following scenarios:
  Group 1: Development of a clinically recognized complication with potential immune etiology or ramifications. Examples include opportunistic infection, rejection, malignancy, alloantibody formation, or immunosuppressive drug toxicity.
  Group 2: Maintenance of immune stability characterized by stable graft function without evident complication. These patients served as comparators for individuals with specific complications under scenario 1. These individuals were enrolled to establish demographically matched cohorts of up to 20 individuals for each identified complication identified in Group 1.
  Group 3: Pre-transplant status. Recipient candidates for kidney, pancreas, liver or lung transplantation were enrolled and they were followed through the waiting period, transplantation and post transplantation. These individuals served to prospectively capture immune complications prior to clinical presentation of an immune complication to facilitate the retrospective evaluation of assays with potential utility in the prospective, sub-clinical detection of burgeoning complications.
  Group 4: Donors for individuals meeting the criteria for one of the 3 above mentioned scenarios. As many of the immune related complications are triggered by or involve immune responses that are specific for donor antigens, donor tissue ease required for the assessment of donor specific immunity. As kidney transplant recipients received organs from live donors, their donors were enrolled to provide target peripheral blood lymphocytes for mechanistic analysis.
  Group 5: Individuals with liver, renal, or pulmonary diseases that may lead to the development of organ failure. Including these individuals allowed the study of mechanisms of diseases that may recur post transplantation, and better enable one to predict which patients are at increased risk for recurrence. Moreover, this group allowed the study of disease complications that may affect the post transplantation course.
  Group 6: Normal volunteers and people on immunosuppressive agents for non-transplanted conditions were recruited to serve as reference comparators for patient samples.

Patients were recruited in a manner that was sensitive to the inclusion of women and members of underserved minority groups. Enrollment targeted demographics that generated a collection of samples from individuals of age, gender, and ethnicity as appropriate for the disease process under evaluation.

Procedure

Following enrollment volunteers were able to donate samples. In general, the volume of blood donated for this study was 50 mL or 3 mL/kg, whichever was less, for each time point. Under circumstances where the needs of a specific assay require larger amounts (e.g., in lymphocyte depleted patients, or multiple planned assays), a larger blood volume, up to a maximum of 150 mL for any single phlebotomy session was collected and did not exceed 3 mL/kg. The total amount of blood drawn did not exceed 450 mL, or 7 mL/kg whichever was less, over any 6-week period in keeping with current NIH guidelines. Biopsy tissue and BAL fluid was limited to tissue or fluid in excess of that required for clinical diagnostic needs, as determined by the physician overseeing the procedure. Urine was limited to that which can be donated without interfering with diagnostic testing, and was typically only collected from normal volunteers and kidney donors or recipients. The donation schedule varied by group. In general, patients with documented complications (Group 1) were enrolled and studied at the time the complication was diagnosed, 1 and 6 months following the resolution (or persistence in the case of chronic conditions) of the complication.

Samples were delivered to the Emory Transplant Biorepository where it was processed for study or storage. In general, blood samples were be separated and stored in the form of peripheral blood mononuclear cells (PBMC), serum, plasma, PBMC derived DNA, and PBMC derived RNA converted to cDNA. Biopsy tissue was snap frozen in liquid nitrogen and converted to DNA, RNA, and cDNA. BAL fluid was separated into a cellular fluid and mononuclear cells, and cells were stored or converted to DNA, RNA, and cDNA. Urine was spun and separated in to a cellular supernatants and cell pellets. Pellets were stored and/or converted to RNA and cDNA. Samples may have been studied fresh or discarded as excess.

Demographic data including age, gender, and race was recorded to assure diversity of this population. Clinical information was collected at the time of each sample collection and included information such as primary disease requiring transplant, date of transplant, date of sample donation, medication dose at time of transplant, most recent level of immunosuppressants, creatinine at time of donation, and baseline creatinine. Each time a subject was asked to donate blood their health status will be reviewed. Clinically concerning information that becomes apparent as a result of study visits (e.g., excessive bruising post phlebotomy, gross hematuria, etc.) was relayed to the patient's attending physician for disposition.

Assay

Peripheral blood samples obtained prior to drug administration and analyzed by multiparameter flow cytometry, specifically analyzing the samples for markers of memory, differentiation, activation, exhaustion and senescence.

The PBMC samples were thawed and resuspended at $5 \times 10^5$ cells/SOW/tube. 1 µl live/dead fixable aqua dead cell stain was added per tube. The tubes were then incubated in the dark at room temperature for 30 mins and then washed 2 times with 1 ml 1×PBS and resuspended in 50 µl of PBS.

Antibodies: The antibodies conjugated to fluorescein isothiocyanate (FITC) included CD2 (BD Pharmingen #555326), CD11a (BioLegend #301206), CD39 (Miltenyi Biotec #130-093-502), CD57 (BD Pharmingen #555619), CD103 (Beckman Coulter #IM1856U), IgD (BD Pharmingen #555778), Ki67 (BD Pharmingen #556026), and Perforin (BD Pharmingen #556577).

The antibodies conjugated to phycoerythrin (PE) included CD25 (Miltenyi Biotec #130-091-024), CD28 (BD Pharmingen #555729), CD31 (Miltenyi Biotec #130-092-653), CD38 (BD Pharmingen #555460), BCL2 (BD Pharmingen #556535), IgM (BD Pharmingen #555783), PD1 (CD279) (BioLegend #329906) and Granzyme B (Invitrogen #MHGB04).

PE-Cy7 is a tandem fluorochrome composed of R-phycoerythrin (PE), which is excited by 488-nm light and serves as an energy donor, coupled to the cyanine dye Cy7(Cy7), which acts as an energy acceptor and fluoresces maximally at 780 nm. The antibodies conjugated to PE-Cy7 tandem fluorochrome included CD19 (BD Pharmingen #341093), CD127 (eBioscience #25-1278-42), and CCR7(CD197) (BD Pharmingen #557648).

The antibodies conjugated to allophycocyanin (APC) included CD27 (BioLegend #302810), HLADR (BD Pharmingen #340549), CCR5(CD195) (R&D #FAB1802A), and IgG (BD Pharmingen #550931). CD127 (BD Pharmingen #558598) was conjugated to ALEXA FLUOR®647. ALEXA FLUOR®647 fluorochrome emission is collected at the same instrument settings as for APC.

The antibodies conjugated to ALEXA FLUOR®700 included CD3 (BD Pharmingen #557943), and CD27 (eBioscience #50-168-83).

The antibodies conjugated to APC-eFluor 780 CD8 (eBioscience #47-0088-42) and CD24 (eBioscience #47-0247-42).

The antibodies conjugated to V450 included CD4 (BD Horizon #560345) and CD5 (BD Horizon #644487).

The antibodies conjugated to Pacific Orange (PacOrange) included CD3 (Invitrogen #CD0330TR), CD14 (Invitrogen #MHCD1430) and CD20 (Invitrogen #MHCD2030).

The antibodies conjugated to QDOT®655 nanocrystal conjugate (QDOT®655) included CD45RA (Invitrogen #Q10069). CD38 (eBioscience #95-0388-42) was conjugated to eFluor650NC. eFluor650NC fluorochrome emission is collected at the same instrument settings as for QDOT®655.

The Extracellular Stain: The required amount of antibodies listed in FIG. 4 were added to the appropriate tubes and incubated in the dark on ice for 30 mins, then washed 2 times with 1 ml 1×PBS and resuspended in 200 µl of PBS.

The Intracellular Stain: 300 µl BD CYTOFIX®/CYTOPERM® was added to tubes 7 and 8 and incubated in the dark, on ice for 30 mins and then washed 2 times with 1 ml 1×BD Perm/Wash buffer. ICS antibodies shown in FIG. 4 were added to the appropriate tubes and incubated in the dark at room temperature for 30 mins, then washed 2 times with 1 ml 1×BD Perm/Wash buffer and resuspended in 200 µl of PBS.

The samples were run on a BD LSRFortessa (BD Biosciences, San Jose, Calif.) according to the manufactures instructions.

PCR analysis of telomere length, a parameter relevant to senescence, also was performed with QuantStudio (Life Technologies) with iTaq SYBR® (Bio-Rad) and compared to reference samples from 5 normal healthy controls. Within 7 months of transplantation, 9 patients experienced acute cellular rejection and 5 were rejection-free.

Results: Patients who eventually experienced acute cellular rejection had a markedly higher percentage of CD4+ CD57+PD1− T cells (p=0.0055) at the time of transplantation compared to patients without rejection (FIG. 1). Although typically considered a marker of senescence, CD57 expression on CD4+ T cells was paradoxically correlated with expression of the proliferation marker Ki67 (p=0.0087), and was not associated with shorter telomere length (p=0.7424). These relationships were limited to the CD4 compartment. CD8+CD57+ T cells marginally trended higher in acute cellular rejection patients (p=0.2358, FIG. 1), but CD57 expression on CD8+ T cells was associated with more traditional indices of senescence including reduced Ki67 expression and shorter telomere length.

Discussion: This study identified a CD4+ T cell phenotype that strongly correlates with risk for belatacept-resistant rejection. CD57 has been commonly described as an external marker of cell senescence, a state in which the cell is in persistent cell cycle arrest. However, the non-senescent (Ki67+, normal telomere length) phenotype associated with CD57, and its limitation to CD4+ T cells suggests that in this setting it is a FLAG® for activated T follicular helper (TFH) cells. TFH cells are antigen-experienced cells known to be critical for certain immune responses and driven by alternative costimulatory pathways including CD154 and the CD28 homologue ICOS.

What is claimed is:

1. A method of treating a transplant patient at risk of costimulation blockade therapy rejection, the method comprising:
   (a) providing a transplant patient or a patient in need of a transplant having at least a 2-fold increase in CD4+ CD57+T cells as compared to a normal healthy control; and
   (b) administering belatacept to the transplant patient
   wherein belatacept is administered to the transplant patient pursuant to an early phase regimen and a maintenance phase regimen;
   wherein the early phase regimen comprises administering 10 mg/kg of belatacept to the transplant patient during the first three to six months post-transplantation; and
   wherein the maintenance phase regimen comprises administering 5 mg/kg of belatacept monthly to the transplant patient following the early phase regimen and continuing for the life of the transplant.

2. The method according to claim 1, wherein the early phase regimen comprises administering belatacept on the day of the transplant, about 96 hours post-transplant, two weeks post-transplant, four weeks post-transplant, eight weeks post-transplant and twelve weeks post-transplant.

3. The method according to claim 2, further comprising administering belatacept sixteen weeks post-transplant, twenty weeks post-transplant and twenty-four weeks post-transplant.

4. The method according to claim 1, wherein the transplant comprises solid organ, tissue and/or cell.

5. The method according to claim 4, wherein the transplant comprises skin, islet cells, muscles, hepatocytes, neurons, heart, liver, kidney, lung, appendages, limbs, nose, ear or face.

6. The method according to claim 4, wherein the transplant is a kidney.

* * * * *

UNITED STATES PATENT AND TRADEMARK OFFICE
CERTIFICATE OF CORRECTION

PATENT NO. : 10,488,413 B2  
APPLICATION NO. : 15/659196  
DATED : November 26, 2019  
INVENTOR(S) : Allan Kirk et al.

Page 1 of 1

It is certified that error appears in the above-identified patent and that said Letters Patent is hereby corrected as shown below:

In the Claims

| Column | Line | |
|---|---|---|
| 15 | 56 (Approx.) | In Claim 1, after "patient" insert -- ; --. |

Signed and Sealed this  
Third Day of March, 2020

Andrei Iancu  
*Director of the United States Patent and Trademark Office*

SEQUENCE LISTING

<160> NUMBER OF SEQ ID NOS: 2

<210> SEQ ID NO 1
<211> LENGTH: 1152
<212> TYPE: DNA
<213> ORGANISM: Artificial
<220> FEATURE:
<223> OTHER INFORMATION: L104EA29YIg

<400> SEQUENCE: 1

| | | | | | |
|---|---|---|---|---|---|
| atgggtgtac | tgctcacaca | gaggacgctg | ctcagtctgg | tccttgcact | cctgtttcca | 60 |
| agcatggcga | gcatggcaat | gcacgtggcc | cagcctgctg | tggtactggc | cagcagccga | 120 |
| ggcatcgcta | gctttgtgtg | tgagtatgca | tctccaggca | aatatactga | ggtccgggtg | 180 |
| acagtgcttc | ggcaggctga | cagccaggtg | actgaagtct | gtgcggcaac | ctacatgatg | 240 |
| gggaatgagt | tgaccttcct | agatgattcc | atctgcacgg | gcacctccag | tggaaatcaa | 300 |
| gtgaacctca | ctatccaagg | actgagggcc | atggacacgg | gactctacat | ctgcaaggtg | 360 |
| gagctcatgt | acccaccgcc | atactacgag | ggcataggca | acggaaccca | gatttatgta | 420 |
| attgatccag | aaccgtgccc | agattctgat | caggagccca | aatcttctga | caaaactcac | 480 |
| acatccccac | cgtccccagc | acctgaactc | ctggggggat | cgtcagtctt | cctcttcccc | 540 |
| ccaaaaccca | aggacaccct | catgatctcc | cggacccctg | aggtcacatg | cgtggtggtg | 600 |
| gacgtgagcc | acgaagaccc | tgaggtcaag | ttcaactggt | acgtggacgg | cgtggaggtg | 660 |
| cataatgcca | agacaaagcc | gcgggaggag | cagtacaaca | gcacgtaccg | tgtggtcagc | 720 |
| gtcctcaccg | tcctgcacca | ggactggctg | aatggcaagg | agtacaagtg | caaggtctcc | 780 |
| aacaaagccc | tcccagcccc | catcgagaaa | accatctcca | aagccaaagg | gcagccccga | 840 |
| gaaccacagg | tgtacaccct | gcccccatcc | cgggatgagc | tgaccaagaa | ccaggtcagc | 900 |
| ctgacctgcc | tggtcaaagg | cttctatccc | agcgacatcg | ccgtggagtg | ggagagcaat | 960 |
| gggcagccgg | agaacaacta | caagaccacg | cctcccgtgc | tggactccga | cggctccttc | 1020 |
| ttcctctaca | gcaagctcac | cgtggacaag | agcaggtggc | agcaggggaa | cgtcttctca | 1080 |
| tgctccgtga | tgcatgaggc | tctgcacaac | cactacacgc | agaagagcct | ctccctgtct | 1140 |
| ccgggtaaat | ga | | | | | 1152 |

<210> SEQ ID NO 2
<211> LENGTH: 383
<212> TYPE: PRT
<213> ORGANISM: Artificial
<220> FEATURE:
<223> OTHER INFORMATION: L104EA29YIg

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

-continued

```
Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380
```